US010094538B2

(12) United States Patent
Smiercik, Jr. et al.

(10) Patent No.: US 10,094,538 B2
(45) Date of Patent: Oct. 9, 2018

(54) LIGHT PROJECTION ASSEMBLY FOR OPACITY MONITORS

(71) Applicant: Teledyne Instruments, Inc., City of Industry, CA (US)

(72) Inventors: Edward A. Smiercik, Jr., Pittsburgh, PA (US); Edward L. McCall, Sewickley, PA (US)

(73) Assignee: TELEDYNE INSTRUMENTS, INC., Thousand Oaks, CA (US)

( * ) Notice: Subject to any disclaimer, the term of this patent is extended or adjusted under 35 U.S.C. 154(b) by 170 days.

(21) Appl. No.: 15/086,791

(22) Filed: Mar. 31, 2016

(65) Prior Publication Data

US 2017/0284936 A1 Oct. 5, 2017

(51) Int. Cl.
*F21V 13/04* (2006.01)
*G01N 21/59* (2006.01)
*F21Y 115/10* (2016.01)

(52) U.S. Cl.
CPC .............. *F21V 13/04* (2013.01); *G01N 21/59* (2013.01); *F21Y 2115/10* (2016.08); *G01N 2201/062* (2013.01); *G01N 2201/0632* (2013.01)

(58) Field of Classification Search
CPC ..................................................... F21V 13/04
USPC ........................................................ 356/437
See application file for complete search history.

(56) References Cited

U.S. PATENT DOCUMENTS

| 2,186,616 | A | * | 1/1940 | Mihalyi | G03B 7/04 |
| | | | | | 359/822 |
| 2,287,785 | A | | 6/1942 | Dean | |
| 3,614,449 | A | * | 10/1971 | Ward | G01S 17/66 |
| | | | | | 250/203.2 |
| 4,360,268 | A | * | 11/1982 | Zucker | G01M 11/35 |
| | | | | | 250/228 |
| 4,937,461 | A | | 6/1990 | Traina | |
| 5,077,480 | A | | 12/1991 | Traina | |
| 5,617,212 | A | | 4/1997 | Stuart | |
| 5,751,423 | A | | 5/1998 | Traina et al. | |
| 5,831,730 | A | | 11/1998 | Traina et al. | |
| 5,963,335 | A | * | 10/1999 | Boutelle | G01N 21/59 |
| | | | | | 356/39 |
| 5,999,257 | A | | 12/1999 | Myers et al. | |
| 6,213,168 | B1 | * | 4/2001 | Gaylo | B22F 3/004 |
| | | | | | 141/12 |
| 6,781,695 | B2 | | 8/2004 | Hovan et al. | |
| 7,715,009 | B1 | | 5/2010 | Myers et al. | |
| 9,074,734 | B2 | | 7/2015 | Tsai et al. | |
| 9,526,150 | B1 | * | 12/2016 | Guan | H05B 37/0227 |

(Continued)

OTHER PUBLICATIONS

40 C.F.R. § 60, Appendix B, Spec. 1, Jul. 1, 2015 edition, pp. 673-684.

(Continued)

*Primary Examiner* — Tarifur Chowdhury
*Assistant Examiner* — Omar Nixon
(74) *Attorney, Agent, or Firm* — K&L Gates LLP

(57) ABSTRACT

The light projection assemblies and opacity monitors described in this specification have an integrating sphere with an input aperture, an output aperture, and a spherical-shaped internal chamber. An LED source is located external to the chamber at the input aperture. A light baffle is located within the chamber at the output aperture. A condenser lens is located external to the chamber at the output aperture.

20 Claims, 16 Drawing Sheets

(56) References Cited

U.S. PATENT DOCUMENTS

| | | | |
|---|---|---|---|
| 2003/0038940 A1* | 2/2003 | Metcalfe | G01N 21/538 356/437 |
| 2006/0187444 A1* | 8/2006 | Tsuchimichi | G01B 11/0625 356/237.1 |

OTHER PUBLICATIONS

Diffuse reflection. In *Wikipedia*, retrieved Jan. 19, 2016 from https://en.wikipedia.org/wiki/Diffuse_reflection.

Fluorilon-99W™, Avian Technologies LLC: Fluorilon, retrieved Jan. 20, 2016 from http://www.aviantechnologies.com/products/coatins/fluorilon.php.

"A Guide to Reflectance Coatings and Materials," Labsphere, pp. 1-25.

"High Reflectance Diffuse Optical Coatings," Avian Technologies LLC: High Reflectance Diffuse Optical Coatings, retrieved Jan. 20, 2016 from http://www.aviantechnolgies.com/products/coatings/highreflectance.php.

Integrating sphere. In *Wikipedia*, retrieved Nov. 12, 2015 from https://en.wikipedia.org/wiki/Integrating_sphere.

"Integrating Sphere Theory and Applications," Labsphere, pp. 1-18.

McKee, Greg, "Integrating Spheres," Photonics Media, retrieved on Nov. 12, 2015 from http://www.photonics.com/EDU/Handbook.aspx?AID=25122.

*LightHawk*® 560ES/560DI Compliance Opacity Monitor Operations Manual, Sep. 2015.

"Optical-grade Spectralon® Reflectance Material," Labsphere, 2015.

Spectralon, In *Wikipedia*, retrieved Jan. 19, 2016 from https://en.wikipedia.org/wiki/Spectralon.

"Standard Practice for Opacity Monitor Manufacturers to Certify Conformance with Design and Performance Specifications," ASTM Int'l, downloaded on Jan. 19, 2016.

* cited by examiner

LIGHT PROJECTION ASSEMBLY FOR OPACITY MONITORS

BACKGROUND

The information described in this background section is not admitted to be prior art.

The United States Environmental Protection Agency, as part of its regulatory mandate under the Clean Air Act, requires the monitoring of particulate emissions from stationary sources such as power plants, manufacturing plants, and the like, to ensure that such sources do not exceed emission limits. Particulate emissions can be monitored by measuring the opacity of gases as they flow through emission stacks or other conduits. In this regard, the measured opacity of gases can be used as an indirect indicator of the level of particulate matter emissions in the gases. The opacity of a gas is defined as the percentage of visible light attenuated due to absorption, reflection, and scattering by particulate matter entrained in the gas (i.e., transparent stack emissions that do not attenuate visible light will have a transmittance of 100 percent and an opacity of zero percent, whereas opaque stack emissions that attenuate all visible light will have a transmittance of zero percent and an opacity of 100 percent). The measurement of the transmittance/opacity of a gas is known as optical transmissometry.

The transmittance/opacity of a gas can be measured using an instrument called an opacity monitor (also known as a transmissometer). Opacity monitors correlate the measured opacity of a gas passing through an emission stack or other conduit to the mass concentration of particulates in the gas. Opacity is measured by projecting a light beam through the gas and determining the difference between the initial intensity of the light beam and the intensity of the light beam which strikes a sensor/detector after having passed through the gas. In single-pass opacity monitors, the sensor/detector is placed on a stack or other conduit wall opposite the light source. In double-pass opacity monitors, a retroreflector is located on the stack or other conduit wall opposite the light source and reflects the light back through the stack or other conduit to a detector positioned near the light source.

SUMMARY

This specification generally relates to opacity monitors and light projection assemblies which may be used in opacity monitors. This specification also relates to methods for monitoring the opacity of gases and methods for projecting light which may be used in methods for monitoring the opacity of gases.

In one example, a light projection assembly comprises an integrating sphere comprising an input aperture, an output aperture, and a spherical-shaped internal chamber. An LED source is located external to the chamber at the input aperture. A light baffle is located within the chamber at the output aperture. A condenser lens is located external to the chamber at the output aperture.

In another example, an opacity monitor comprises a retroreflector assembly and a transceiver assembly. The transceiver assembly is configured to project a light beam to the retroreflector assembly. The retroreflector assembly is configured to reflect the projected light beam back to the transceiver assembly when the transceiver assembly and the retroreflector assembly are optically aligned along a central axis. The transceiver assembly comprises a sensor configured to detect the intensity of the projected and reflected light beam. The transceiver assembly also comprises a light projection assembly configured to produce the light beam. The light projection assembly comprises an integrating sphere comprising an input aperture, an output aperture, and a spherical-shaped internal chamber. An LED source is located external to the chamber at the input aperture. A light baffle is located within the chamber at the output aperture. A condenser lens is located external to the chamber at the output aperture.

In another example, the opacity values measured by the opacity monitors described in this specification vary by no greater than ±0.5% opacity when the transceiver/transmitter assembly or the retroreflector/receiver assembly is angularly misaligned by up to ±0.25 degrees from the central alignment axis at a distance of 3 meters between the transceiver/receiver and the retroreflector/receiver.

It is understood that the invention described in this specification is not necessarily limited to the examples summarized in this Summary.

BRIEF DESCRIPTION OF THE DRAWINGS

Various features and characteristics of the invention described in this specification may be better understood by reference to the accompanying figures, in which.

The reader will appreciate the foregoing features and characteristics, as well as others, upon considering the following detailed description of the invention according to this specification.

DESCRIPTION

In this specification, including the claims, spatial terms (e.g., top, bottom, vertical, horizontal, above, below, over, under, and the like) used to describe the relative orientation, location, or positioning of various components are not to be construed as limited to any specific frame of reference.

As noted above, opacity monitors measure the opacity of a gas by projecting a visible light beam through the gas and determining the difference between the initial intensity of the light beam and the intensity of the light beam which strikes a sensor/detector after having passed through the gas. The difference between the intensities of the projected and detected light beam provides a measure of the attenuation due to absorption, reflection, and scattering by particulate matter entrained in the gas.

Figure 1:
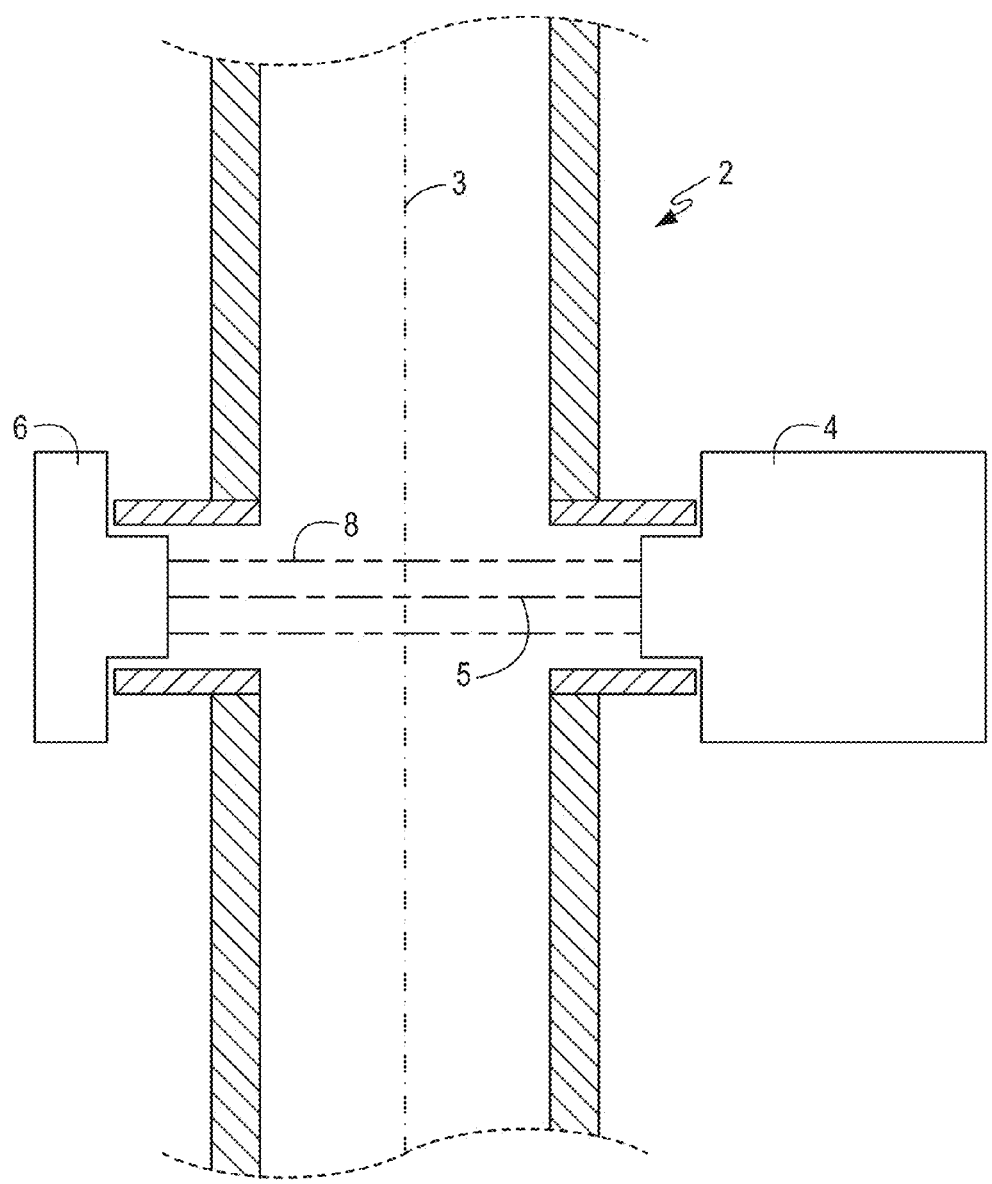
FIG. 1 is a cross-sectional side view schematic diagram of an opacity monitor (single-pass or double-pass) mounted on a stack, duct, or other conduit.

Referring to FIG. 1, an opacity monitor comprises a transceiver/transmitter 4 and a retroreflector/receiver 6. It is noted that a double-pass opacity monitor would comprise a transceiver 4 and a retroreflector 6, whereas a single-pass opacity monitor would comprise a transmitter 4 and a receiver 6. The transceiver/transmitter 4 and the retroreflector/receiver 6 are mounted on opposite sides of a conduit 2. The transceiver/transmitter 4 and the retroreflector/receiver 6 are optically aligned along a central alignment axis 5 which is generally perpendicular to a longitudinal axis 3 of the conduit 2. The transceiver/transmitter 4 projects a collimated beam 8 of visible light across the width of the conduit 2 along the central alignment axis 5. The retroreflector/receiver 6 either detects the intensity of the received light beam 8 (single-pass opacity monitor) or reflects the light beam 8 back across the width of the conduit 2, along the central alignment axis 5, and to the transceiver 4 (double-pass opacity monitor) which detects the intensity of the reflected light beam.

The United States Environmental Protection Agency (US-EPA) has promulgated regulations at 40 C.F.R. § 60, Appendix B, Performance Specification 1—*Specifications and Test Procedures for Continuous Opacity Monitoring Systems in Stationary Sources* (2015), which establish the operational requirements for opacity monitors. The version of US-EPA's Performance Specification 1 (40 C.F.R. § 60, Appendix B) currently in force incorporates by reference ASTM D6216-98: *Standard Practice for Opacity Monitor Manufacturers to Certify Conformance with Design and Performance Specifications*. The US-EPA's Performance Specification 1 (40 C.F.R. § 60, Appendix B) requires that opacity monitors conform to and meet the design and performance specifications in ASTM D6216-98.

ASTM International originally published ASTM D6216 in 1998. ASTM International published new versions of ASTM D6216 in 2003, 2007, and 2012, each superseding the prior versions. Notwithstanding the newer versions of ASTM D6216, the version of US-EPA's Performance Specification 1 currently in force incorporates by reference and requires conformance to the original 1998 version of ASTM D6216-98. However, the US-EPA is expected to soon amend the Performance Specification 1 (40 C.F.R. § 60, Appendix B) to incorporate by reference the 2012 version of ASTM D6216-12. ASTM D6216-12: *Standard Practice for Opacity Monitor Manufacturers to Certify Conformance with Design and Performance Specifications*, published November 2012, is incorporated by reference into this specification.

ASTM D6216-12, Annex A1, establishes more restrictive performance specifications for opacity monitors that are intended for use in environments with expected opacity values of less than 10% (i.e., low level opacity monitors). Such performance specifications include the off-axis performance specifications set forth in ASTM D6216-12 Annex A1.3.7: *Transceiver or Transmitter Misalignment*, Annex A1.3.8: *Reflector or Receiver Misalignment*, and Annex A1.3.9: *Lateral Misalignment*.

The off-axis performance specifications set forth in ASTM D6216-12, Annex A1.3.7 and Annex A1.3.8, requires that the opacity values measured by an opacity monitor vary by no greater than ±0.5% opacity when the transceiver/transmitter or the retroreflector/receiver is angularly misaligned by up to ±0.25 degrees from the central alignment axis at a flange-to-flange distance of 3 meters between the transceiver/transmitter and the retroreflector/receiver (i.e., a 3 meter pathlength). The off-axis performance specification set forth in ASTM D6216-12, Annex A1.3.9, requires that the opacity values measured by an opacity monitor vary by no greater than ±0.5% opacity when the transceiver/transmitter or the retroreflector/receiver is laterally misaligned from the central alignment axis by a distance of up to ±)tan(0.25° times the 3 meter pathlength (i.e., ±13 millimeter).

In other words, ASTM D6216-12, Annex A1.3.7, Annex A1.3.8, and Annex A1.3.9, requires that opacity monitors exhibit a change of <0.5% opacity during operation for a ±0.25° rotational misalignment, and a ±13 millimeter linear misalignment, of either the transceiver/transmitter or the retroreflector/receiver, at a 3 meter pathlength between the transceiver/transmitter and the retroreflector/receiver.

To measure off-axis performance due to rotational misalignment of a transceiver/transmitter, ASTM D6216-12, Annex A1.3.7, specifies tilting the transceiver/transmitter upward in the vertical plane relative to the retroreflector/receiver until an error of ±0.5% opacity is first indicated on the instrument's data recorder, and verifying that the instrument's alignment indicator shows misalignment and that the misalignment is greater than 0.25 degrees off-axis. Similarly, to measure off-axis performance due to lateral misalignment of a retroreflector/receiver, ASTM D6216-12, Annex A1.3.9, specifies slowly moving the retroreflector/receiver linearly relative to the transceiver/transmitter until an error of ±0.5% opacity is first indicated on the instrument's data recorder, and verifying that the instrument's alignment indicator shows misalignment and that the misalignment is greater than)tan(0.25° times the pathlength off-axis (i.e., 13 millimeter for a 3 meter pathlength).

It is noted that for double-pass opacity monitors, measurement of off-axis performance due to rotational misalignment of a retroreflector does not provide meaningful results because a retroreflector does not displace the optical return beam when tilted relative to the transceiver. Therefore, for double-pass opacity monitors, off-axis performance is measured in accordance with ASTM D6216-12, Annex A1.3.7 and Annex A1.3.9. However, for single-pass opacity monitors, off-axis performance is typically measured in accordance with ASTM D6216-12, Annex A1.3.7, Annex A1.3.8, and Annex A1.3.9. Measurement of off-axis performance in accordance with ASTM D6216-12, Annex A1.3.8 is conducted analogous to Annex A1.3.7, only the receiver is tilted upward in the vertical plane relative to the transmitter until an error of ±0.5% opacity is first indicated on the instrument's data recorder, and verifying that the instrument's alignment indicator shows misalignment and that the misalignment is greater than 0.25 degrees off-axis.

For the off-axis performance measurements under ASTM D6216-12, Annex A1.3.7, Annex A1.3.8, and Annex A1.3.9, the transceiver/transmitter and retroreflector/receiver initially should be optically aligned along a central alignment axis at a flange-to-flange pathlength distance of 3 meters. As used herein, "flange-to-flange distance" means the distance between the outside face of a mounting flange that supports a transceiver/transmitter and the outside face of a mounting flange that supports a retroreflector/receiver. Mounting flanges are devices used to attach transceivers/transmitters and retroreflectors/receivers to the access ports in the walls of stacks, ducts, or other conduits.

Figure 2A:
FIGS. 2A-2C are schematic diagrams illustrating the optical misalignment of the transceiver and the retroreflector of a double-pass opacity monitor.

Referring to FIG. 2A, an opacity monitor comprises a transceiver 14 optically aligned with a retroreflector 16 along a central alignment axis 15. The transceiver 14 projects an output beam 18 of visible light toward the retroreflector 16 along the central alignment axis 15. The retroreflector 16 reflects a return beam 19 back along the central alignment axis 15 to the transceiver 14. As shown in FIG. 2A, the transceiver 14 and the retroreflector 16 have a zero degree off-axis rotational misalignment and a zero off-axis lateral misalignment relative to the central axis 15.

Figure 2B:
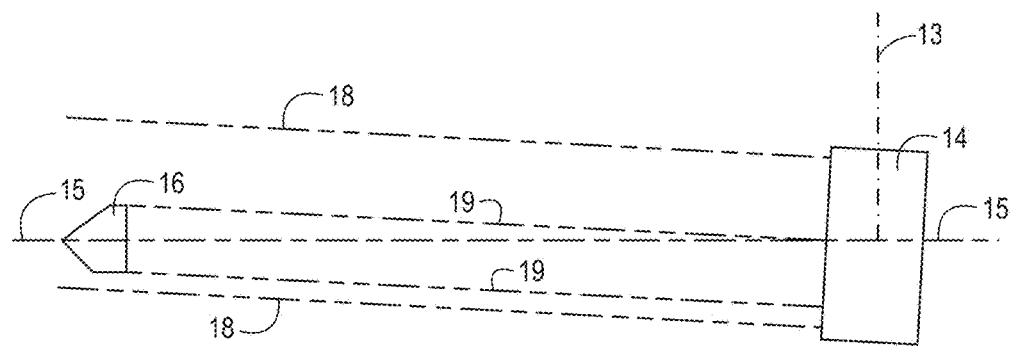

Referring to FIG. 2B, the transceiver 14 has a non-zero degree rotational misalignment off-axis from the central axis 15, in which the transceiver 14 is tilted upward in the vertical plane defined by the central axis 15 and the normal (vertical) axis 13. As shown in FIG. 2B, the output beam 18 is misaligned off-axis from the central axis 15. As described above, in order to comply with the requirements of ASTM D6216-12, Annex A1.3.7, if the transceiver 14 is misaligned by up to 0.25 degrees from the central axis 15, then any change in measured opacity value relative to the opacity value measured during the condition illustrated in FIG. 2A must be less than or equal to 0.5% opacity.

Figure 2C:
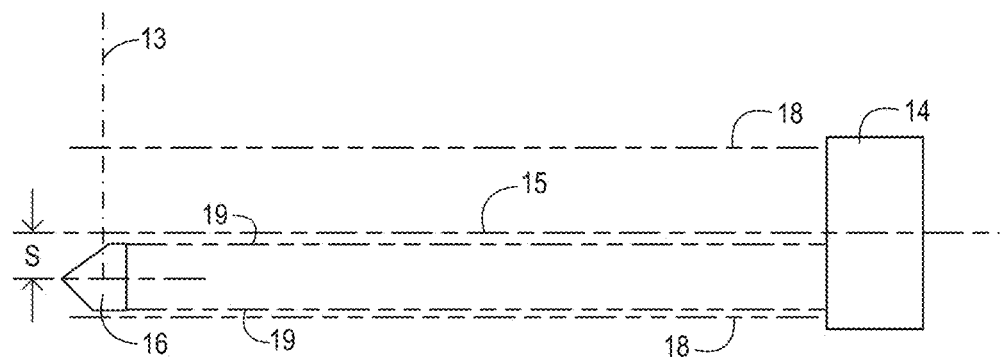

Referring to FIG. 2C, the retroreflector 16 has a lateral misalignment off-axis from the central axis 15, in which the retroreflector 16 is translated off the central axis 15 along the normal axis 13. As shown in FIG. 2C, the return beam 19 is misaligned off-axis from the central axis 15. As described above, in order to comply with the requirements of ASTM D6216-12, Annex A1.3.9, if the retroreflector 16 is misaligned from the central axis 15 by a distance S that is less than or equal to tan(0.25°) times the transceiver-to-retroreflector pathlength (i.e., 13 millimeter for a 3 meter pathlength), then any change in measured opacity value relative to the opacity value measured during the condition illustrated in FIG. 2A must be less than or equal to 0.5% opacity.

Figure 3A:
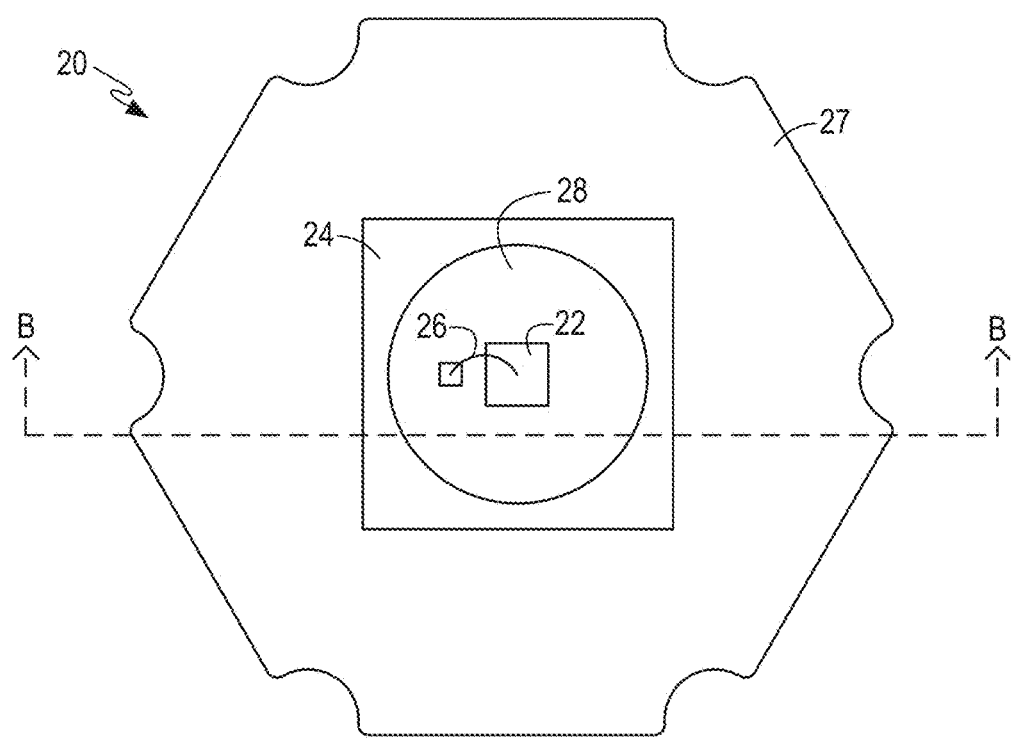
FIG. 3A is a top view schematic diagram of a single-die light emitting diode (LED) source.
Figure 3B:
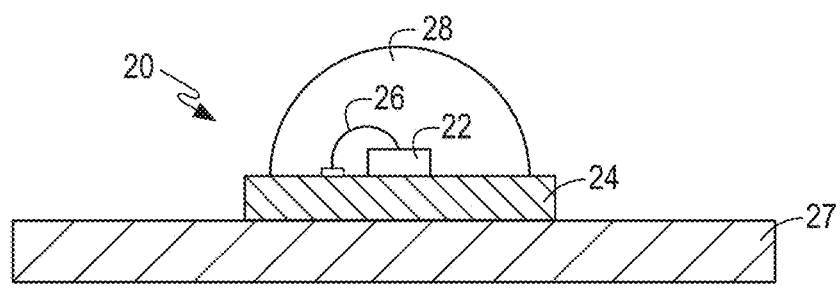
FIG. 3B is a cross-sectional side view along line B-B in FIG. 3A.

The off-axis performance requirements set forth in ASTM D6216-12, Annex A1.3.7, Annex A1.3.8, and Annex A1.3.9, are difficult to achieve using light emitting diode (LED) sources for the projected output beam. While not intending to be bound by theory, it is believed that this difficulty is caused, at least in part, by shadows, light gaps, or other light obscurities resulting from the structure of the LEDs. For example, referring to FIGS. 3A and 3B, an LED source 20 comprises a single die 22 electrically bonded to an emitter plate 24 with a wire 26. The emitter plate 24 is connected to a printed circuit board or other substrate 27. The die 22 and the wire 26 are encapsulated between the emitter plate 24 and a lens 28. The wire 26 blocks a portion of the light emitted from the LED die 22, casting a shadow on the lens 28 and creating an obscurity in the light output from the LED source 20.

Figure 4A:
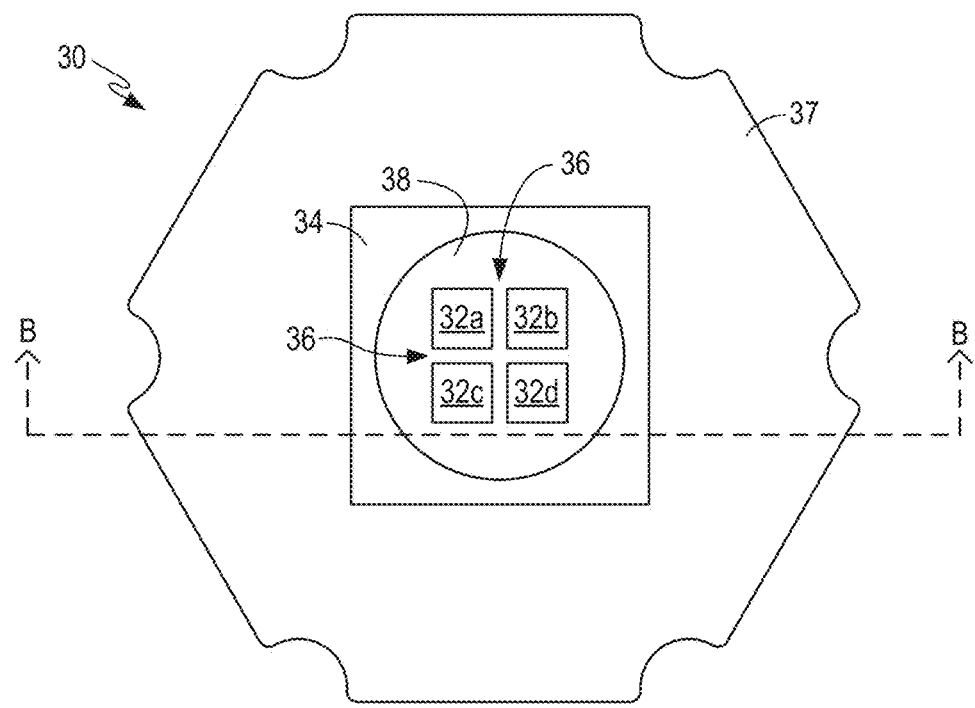
FIG. 4A is a top view schematic diagram of a multiple-die (four dies) LED source.
Figure 4B:
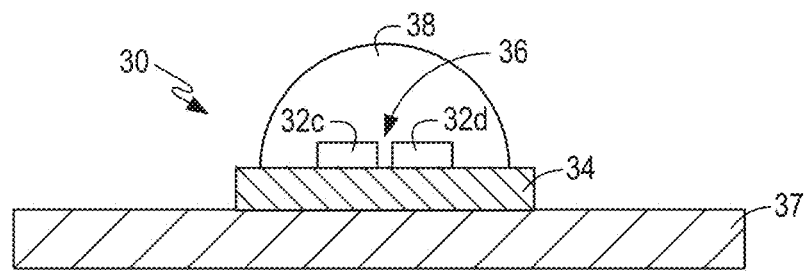
FIG. 4B is a cross-sectional side view along line B-B in FIG. 4A.

Similarly, referring to FIGS. 4A and 4B, an LED source 30 comprises multiple dies 32*a*-32*d* electrically bonded to an emitter plate 34 (electrical bonds not shown). The emitter plate 34 is connected to a printed circuit board or other substrate 37. The dies 32*a*-32*d* are encapsulated between the emitter plate 34 and a lens 38. The dies are arrayed with gaps 36 located between adjacent dies—i.e., gaps 36 between dies 32*a* and 32*b*, 32*a* and 32*c*, 32*b* and 32*d*, and 32*c* and 32*d*. The gaps 36 cast dark lines on the lens 38 and create obscurities in the light output from the LED source 30.

It is believed that the obscurities in the light output from both single-die and multi-die LED sources may prevent opacity monitors comprising such LED sources from meeting the off-axis performance requirements set forth in ASTM D6216-12, Annex A1.3.7, Annex A1.3.8, and Annex A1.3.9. Opacity monitors comprising LED sources and optical (glass) diffusers may still fail to meet the off-axis performance requirements set forth in ASTM D6216-12, Annex A1.3.7, Annex A1.3.8, and Annex A1.3.9. In fact, the inventors observed that systems in which LED light output was passed through an optical diffuser before projecting from the transceiver/transmitter of an opacity monitor failed to reliably achieve the <0.5% opacity change for a ±0.25° rotational misalignment and a ±13 millimeter lateral misalignment of either the transceiver/transmitter or the retroreflector/receiver.

Opacity monitors comprising a light projection assembly comprising an integrating sphere may meet the off-axis performance requirements set forth in ASTM D6216-12, Annex A1.3.7, Annex A1.3.8, and Annex A1.3.9, even when the light projection assembly also comprises a single-die or multi-die LED source. Referring to FIGS. 5A-5E, a light projection assembly 50 comprises an integrating sphere 52. The integrating sphere 52 comprises an input aperture 54, an output aperture 56, and a spherical-shaped internal chamber 58. An LED source 60 is located external to the chamber 58 at the input aperture 54. A light baffle 72 is located within the chamber 58 at the output aperture 56. A condenser lens 80 is located external to the chamber 58 at the output aperture 56.

The integrating sphere 52 comprises a sphere housing 53. The spherical-shaped internal chamber 58 is formed inside the sphere housing 53 and is surrounded by a spherical-shaped internal surface 55. The input aperture 54 extends between the internal surface 55 of the sphere housing 53 and an external surface 51 of the sphere housing 53. The output aperture 56 extends through a baffle ring 70. The baffle ring 70 is located in an output port 57 (see FIGS. 5D and 5E) extending between the internal surface 55 of the sphere housing 53 and the external surface 51 of the sphere housing 53.

The input aperture 54 comprises an input area, and the output aperture 56 comprises an output area. For example, if the input aperture 54 and the output aperture 56 have circular cross-sectional shapes, then the input area is the area of the smallest circular cross-section of the input aperture, and the output area is the area of the smallest circular cross-section of the output aperture. The sum of the input area and the output area may be less than 5% of the total surface area of the chamber 58 (i.e., the sum of the input area and the output area may be less than 5% of the area of the spherical-shaped internal surface 55 plus the input area plus the output area).

Figure 6A:
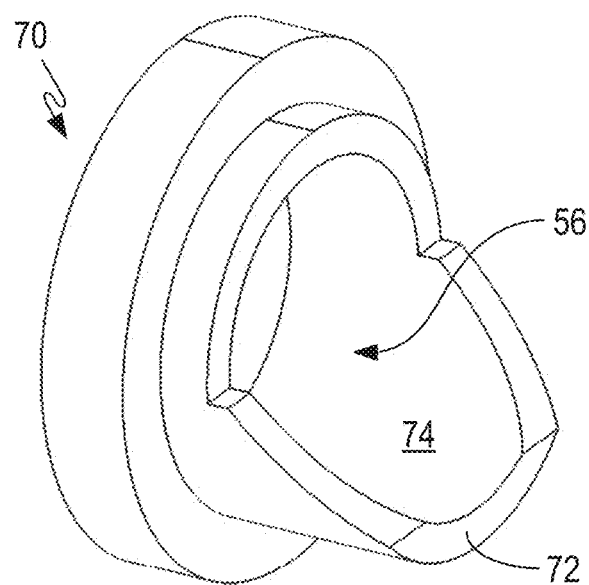
FIGS. 6A and 6B are perspective views of a baffle ring comprising an integrally-formed light baffle.
Figure 6B:
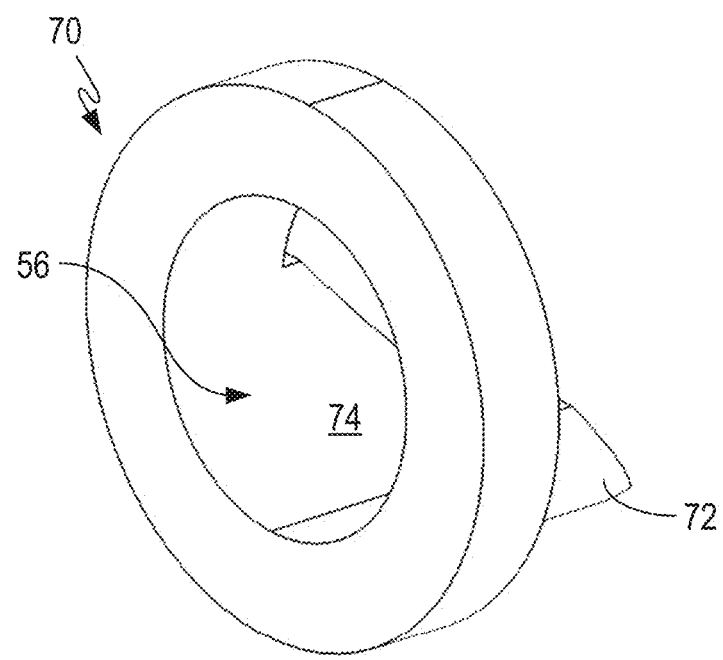

The light projection assembly 50 further comprises the baffle ring 70 located in the output port 57 (see FIGS. 5D and 5E) through the wall of the sphere housing 53 of the integrating sphere 52 (extending between the internal surface 55 and the external surface 51). The output aperture 56 extends through the baffle ring 70 and connects the spherical-shaped internal chamber 58 to a region external to the integrating sphere 52. Referring to FIGS. 6A and 6B, the light baffle 72 is integrally formed on the baffle ring 70. The light baffle 72 comprises a semi-cylindrical shaped surface 74 surrounding a portion of the output aperture 56. The baffle ring 70 is a structural component that is separate from, but attachable to, the integrating sphere 52. The baffle ring 70 may be located in the output port 57 and attached to the integrating sphere 52 using fasteners or adhesives, for example. Alternatively, the outside dimensions and the baffle ring 70 and the inside dimensions of the output port 57 may be sized for the compression fitting of the baffle ring 70 into the integrating sphere 52. Alternatively or additionally, the baffle ring 70 may be held in place in the output port 57 of the integrating sphere 52 by contact with an attached projection housing (see FIGS. 8 and 9).

Figure 7:
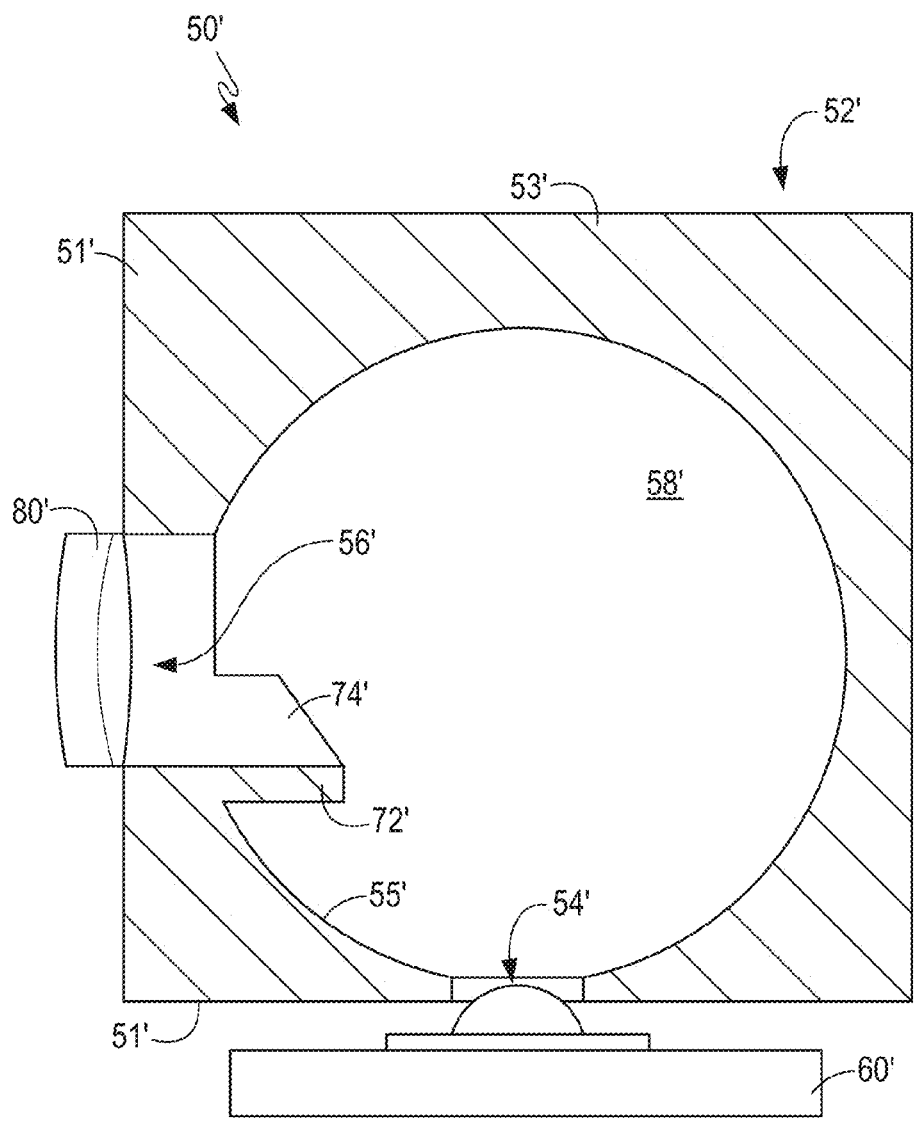
FIG. 7 is a cross-sectional side view schematic diagram of a light projection assembly comprising an integrating sphere with an input aperture, an output aperture, and a spherical-shaped internal chamber, an LED source located external to the chamber at the input aperture, a condenser lens located external to the chamber at the output aperture, and a light baffle located within the chamber at the output aperture, the light baffle integrally-formed on an internal surface of the spherical-shaped internal chamber.

The light baffle 72 shown in FIGS. 5A-5C, 6A, and 6B is integrally formed on the baffle ring 70. Alternatively, a separate baffle ring may be omitted and a light baffle integrally formed on the internal surface of the internal chamber of an integrating sphere. Referring to FIG. 7, a light projection assembly 50' comprises an integrating sphere 52'. The integrating sphere 52' comprises an input aperture 54', an output aperture 56', and a spherical-shaped internal chamber 58'. An LED source 60' is located external to the chamber 58' at the input aperture 54'. A light baffle 72' is located within the chamber 58' at the output aperture 56'. The light baffle 72' is integrally formed on the spherical-shaped internal surface 55' of the chamber 58'. The light baffle 72' comprises a semi-cylindrical shaped surface 74' surrounding a portion of the output aperture 56'. A condenser lens 80' is located external to the chamber 58' at the output aperture 56'.

The integrating sphere 52' comprises a sphere housing 53'. The spherical-shaped internal chamber 58' is formed inside the sphere housing 53' and is surrounded by the spherical-shaped internal surface 55'. The input aperture 54' and the output aperture 56' each extend between the internal surface 55' of the sphere housing 53' and an external surface 51' of the sphere housing 53'. The input aperture 54' comprises an input area, and the output aperture 56' comprises an output area. The sum of the input area and the output area may be less than 5% of the total surface area of the chamber 58' (i.e., the sum of the input area and the output area may be less than 5% of the area of the spherical-shaped internal surface 55' plus the input area plus the output area).

Figure 5A:
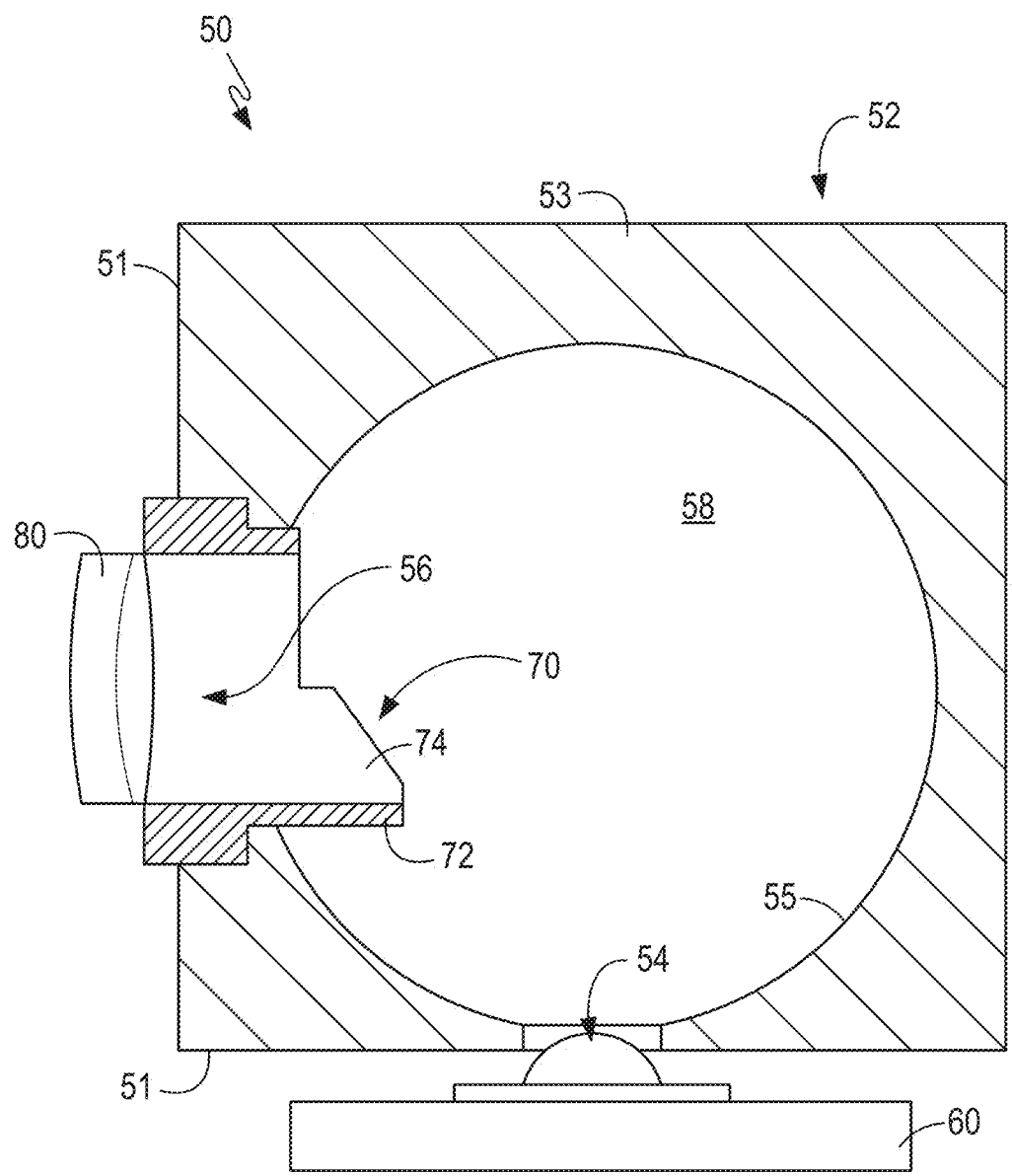
FIGS. 5A-5C are cross-sectional side view schematic diagrams of a light projection assembly comprising an integrating sphere with an input aperture, an output aperture, and a spherical-shaped internal chamber, an LED source located external to the chamber at the input aperture, a light baffle located within the chamber at the output aperture, and a condenser lens located external to the chamber at the output aperture.
Figure 5B:
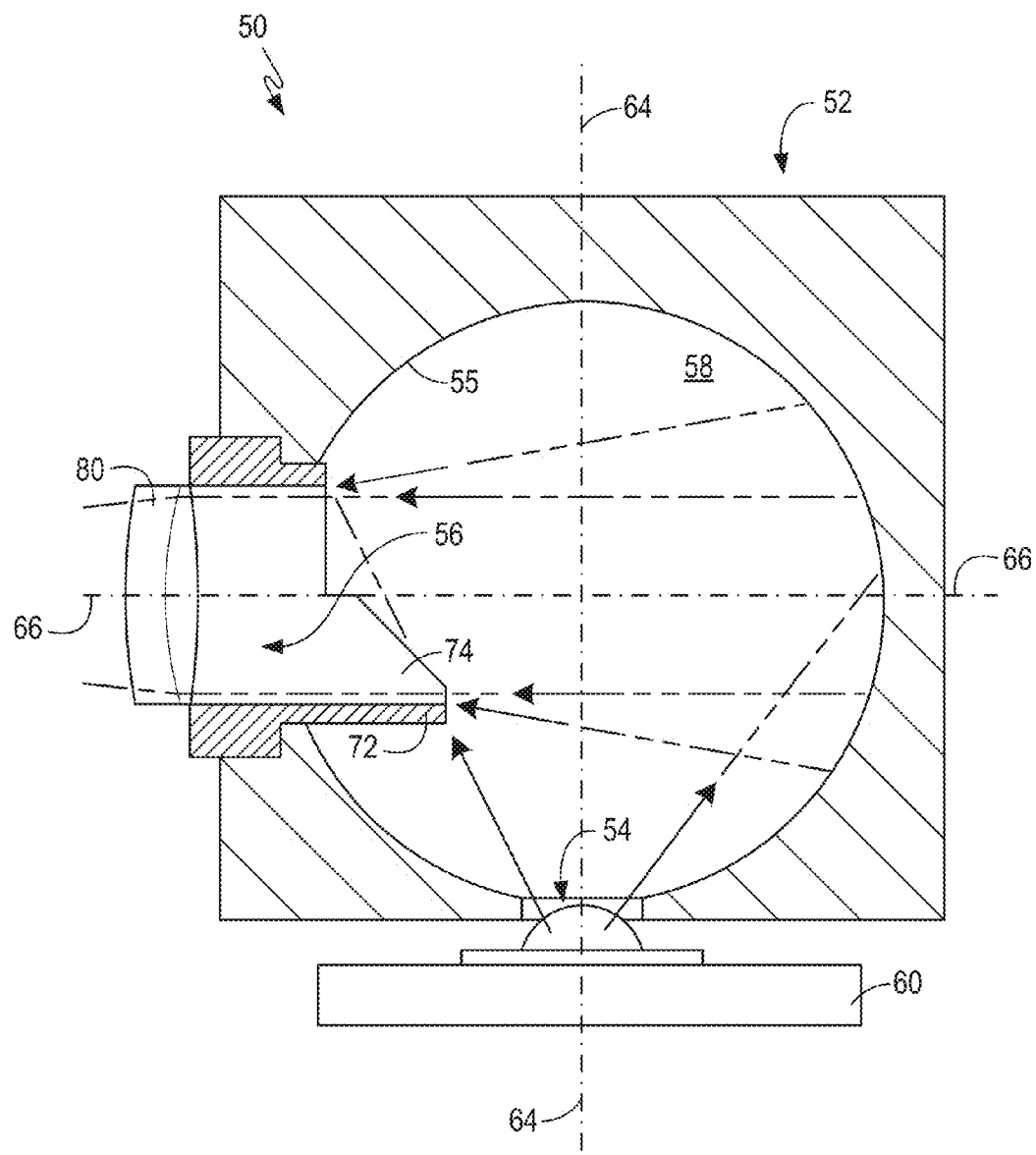

Referring to FIG. 5B, the input aperture 54 comprises an input axis 64, and the output aperture 56 comprises an output axis 66. The input axis 64 is perpendicular to the output axis 66. The light baffle 72 extends from the baffle ring 70 into the spherical-shaped internal chamber 58 parallel to the output axis 66. The semi-cylindrical shaped surface 74 of the light baffle 72 is parallel to the output axis 66. The LED source 60 is located perpendicular to the input axis 64 and light rays emitted from the LED source 60 enter into the spherical-shaped internal chamber 58 through the input aperture 54. The light baffle 72 is shaped and sized so that the light rays entering through the input aperture 54 do not have a line-of-sight directly through the output aperture 56. Instead, the light rays entering through the input aperture 54 must reflect off of the light baffle 72 and/or the internal surface 55, and thereby reflect around the spherical-shaped internal chamber 58 of the integrating sphere 52, before exiting through the output aperture 56.

Figure 5C:
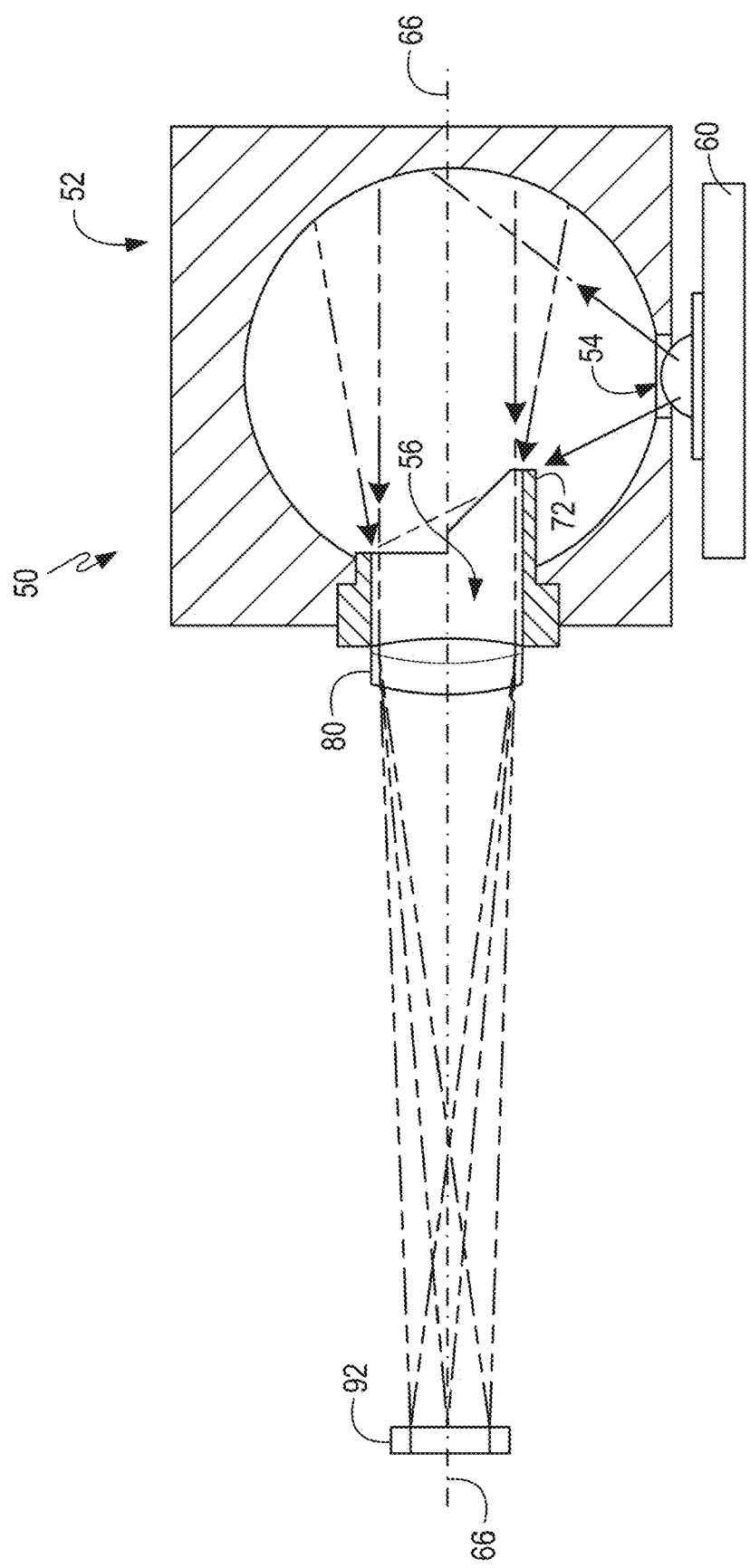
Figure 5D:
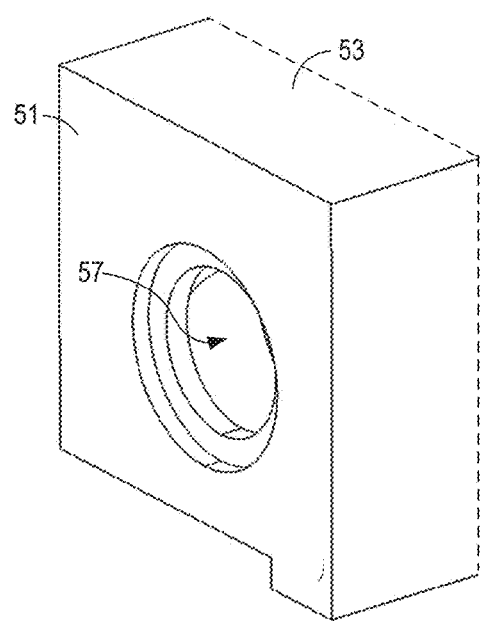
FIGS. 5D and 5E are sectional perspective views of an integrating sphere with an input aperture, an output port, and a spherical-shaped internal chamber.
Figure 5E:
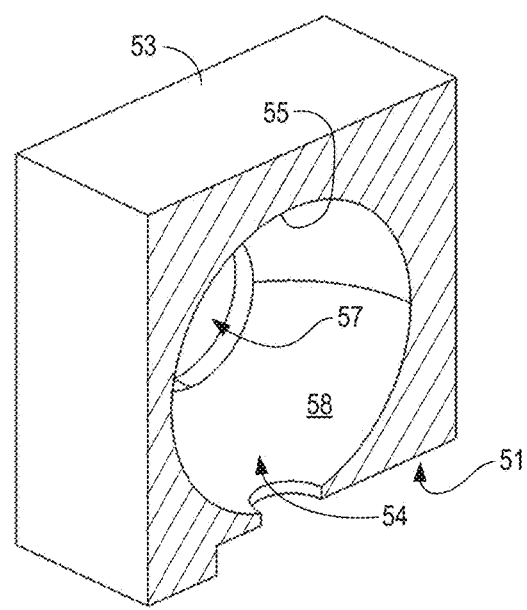

The internal reflection of light rays inside the spherical-shaped internal chamber 58 spatially integrates and homogenizes the light flux from the LED source 60, thereby eliminating any obscurities from the LED source 60, and provides diffuse and uniformly distributed illumination through the output aperture 56. The condenser lens 80 collects the light exiting through the output aperture 56. Referring to FIG. 5C, the light projection assembly 50 may further comprise a projection aperture 92. The condenser lens 80 and the projection aperture 92 are optically aligned along the output axis 66. The condenser lens 80 collects the light exiting through the output aperture 56 and focuses the light onto the projection aperture 92.

The integrating sphere 52, the baffle ring 70, and the baffle 72 shown in FIGS. 5A-6B (including the integrating sphere 52' and the baffle 72' shown in FIG. 7) may comprise a material of construction that provides surfaces with highly diffuse reflectance. For example, the integrating sphere 52/52', the baffle ring 70, and the baffle 72/72' may comprise a material of construction comprising sintered poly(tetrafluoroethylene) (PTFE). Sintered PTFE is produced by pressing PTFE powder into a green compact and sintering the green compact to bind the powder particles together into a solid piece of material. Sintered PTFE can be readily molded or machined into components such as the integrating sphere 52/52', the baffle ring 70, and the baffle 72/72'. Sintered PTFE is commercially available under the trade names FLUORILON (Avian Technologies, LLC) and SPECTRALON (Labsphere, Inc.).

The integrating sphere 52/52', the baffle ring 70, and the baffle 72/72' may comprise a material of construction that does not provide surfaces with highly diffuse reflectance, provided the light-contacting surfaces of the integrating sphere 52/52', the baffle ring 70, and the baffle 72/72' (including the spherical-shaped internal surface 55/55' and the semi-cylindrical shaped surface 74/74') are coated with a material that provides highly diffuse reflectance. For example, the integrating sphere 52/52', the baffle ring 70, and the baffle 72/72' may comprise a material of construction comprising aluminum or plastic coated with a barium-sulfate-based coating such as AVIAN-B or AVIAN-D (available from Avian Technologies, LLC) or SPECTRAFLECT (available from Labsphere, Inc.).

Figure 8:
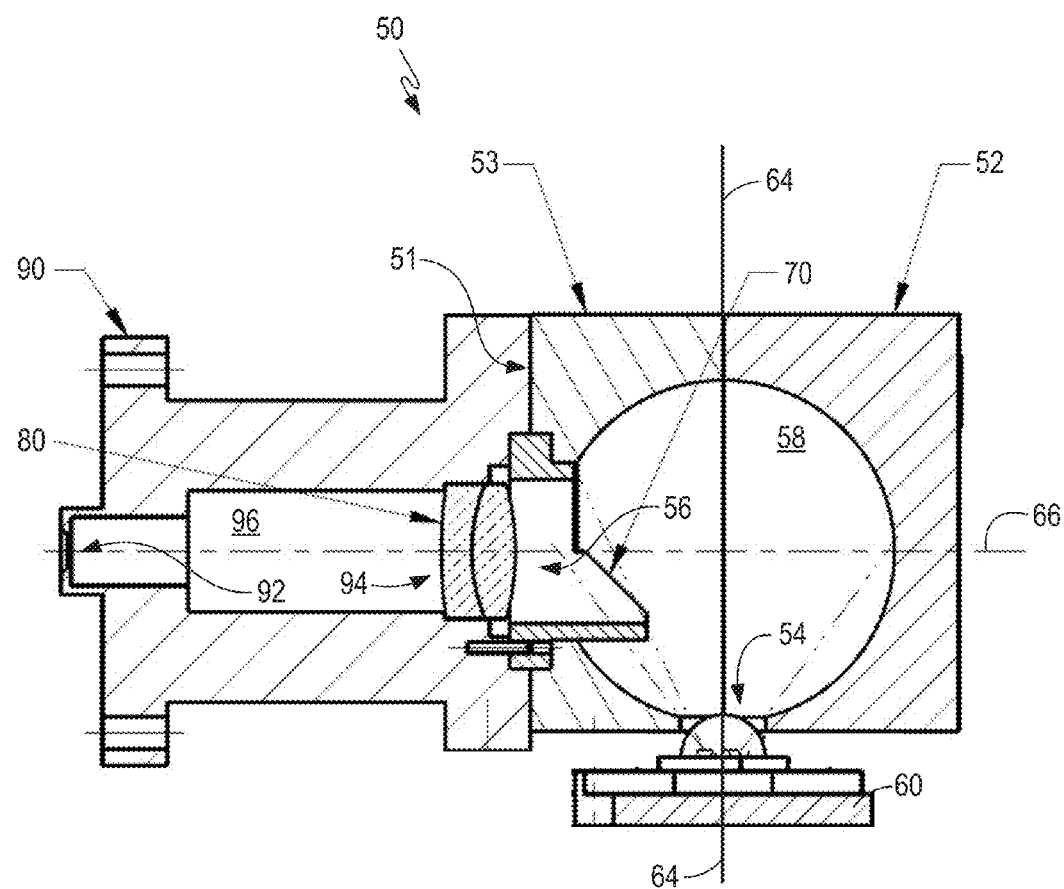
FIG. 8 is a cross-sectional side view of a light projection assembly comprising an integrating sphere attached to a projection housing.
Figure 9:
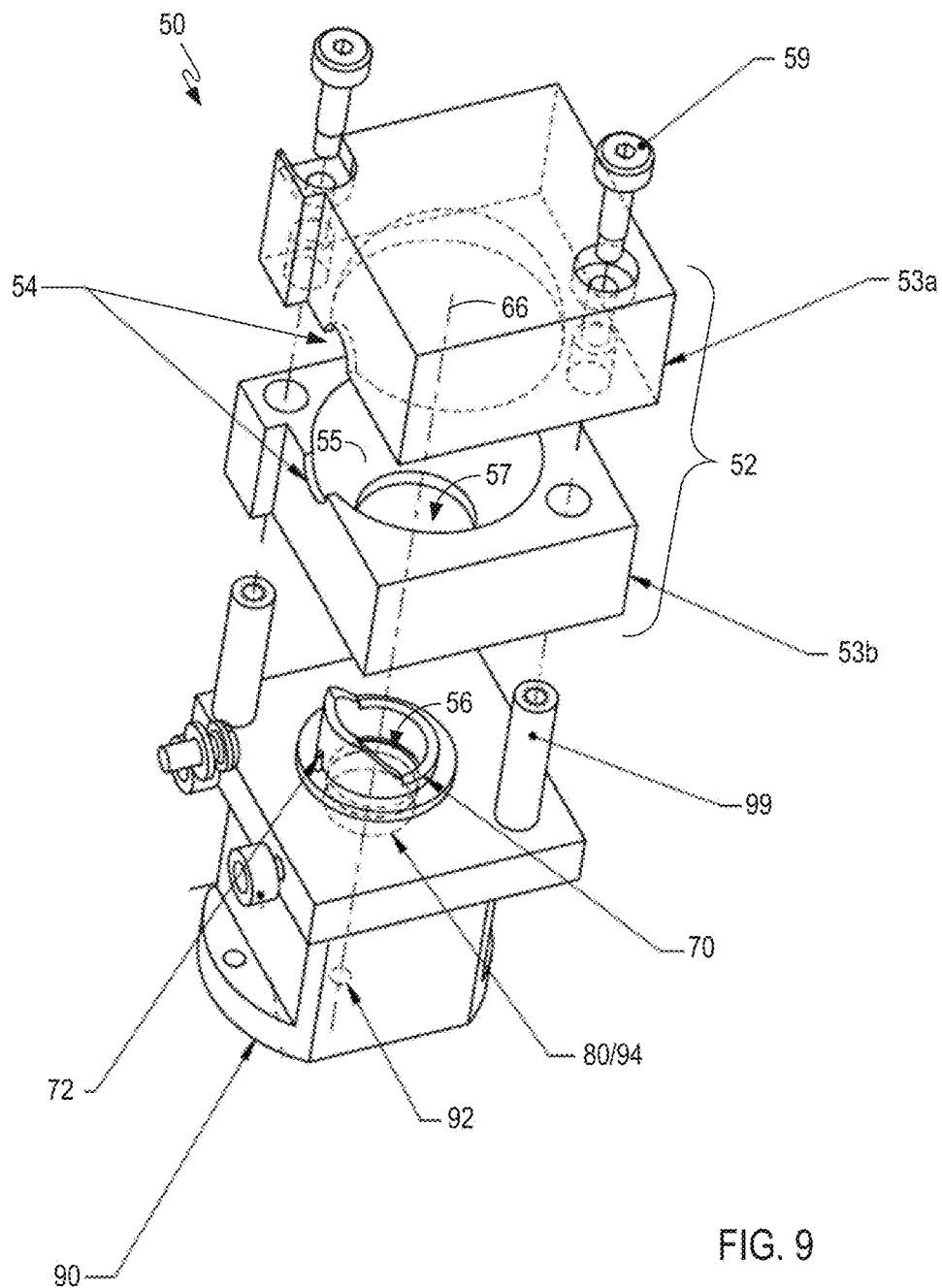
FIG. 9 is an exploded perspective view of a light projection assembly comprising multi-component integrating sphere and a projection housing.

Referring again to FIG. 5C, the condenser lens 80 collects the light exiting through the output aperture 56 of the integrating sphere 52 and focuses the light onto the projection aperture 92. The projection aperture 92 may be formed in a projection housing (not shown) attached to the external surface 51 of the sphere housing 53. Referring to FIG. 8, the light projection assembly 50 may further comprise a projection housing 90. The projection housing 90 is attached to the external surface 51 of the integrating sphere housing 53 adjacent to the output aperture 56. The projection housing 90 may be attached to the integrating sphere housing 53 using fasteners, for example (see FIG. 9).

Still referring to FIG. 8, the projection housing 90 comprises a projection aperture 92, a lens opening 94, and an internal channel 96 between the projection aperture 92 and the lens opening 94. The condenser lens 80 is at least partially located in the lens opening 94 and is optically aligned with the output aperture 56 and the projection aperture 90. The condenser lens 80 collects light exiting from the integrating sphere 52 through the output aperture 56 and focuses the collected light through the projection aperture 92.

The integrating sphere 52/52' shown in FIGS. 5A-5E, 7, and 8 comprises a single sphere housing 53/53'. It is understood, however, that the integrating sphere 52/52' can comprise multiple housing components that together form the integrating sphere 52/52', including the spherical-shaped internal chamber 58/58'. For example, referring to FIG. 9, the integrating sphere 52 comprises two sphere housing components 53a and 53b that attach together to form the integrating sphere 52. The first sphere housing component 53a comprises a first hemispherical portion of the spherical-shaped internal chamber 58 and a first portion of the input aperture 54. The second sphere housing component 53b comprises a second hemispherical portion of the spherical-shaped internal chamber 58, a second portion of the input aperture 54, and the output port 57 extending between the internal surface 55 and the external surface 51 of the integrating sphere 52. The first sphere housing component 53a, the second sphere housing component 53b, and the projection housing 90 can be attached together with positioning standoffs 99 and screw fasteners 59.

An opacity monitor (including either a single-pass or a multi-pass opacity monitor) may comprise the light projection assembly 50/50' illustrated in any of FIGS. 5A-9. An opacity monitor comprising a light projection assembly as described in this specification may measure opacity values that vary by no greater than ±0.5% opacity when the transceiver/transmitter assembly or the retroreflector/receiver assembly is angularly misaligned by up to ±0.25 degrees from the central alignment axis at a flange-to-flange distance of 3 meters between the transceiver/receiver and the retroreflector/receiver, or when the transceiver/transmitter assembly or the retroreflector/receiver assembly is laterally misaligned by up to ±13 millimeter (i.e., 3 meter*tan(0.25°)) from the central alignment axis. Thus, opacity monitors comprising the light projection assembly described in this specification may meet the off-axis performance requirements set forth in ASTM D6216-12, Annex A1.3.7, Annex A1.3.8, and Annex A1.3.9.

Figure 10:
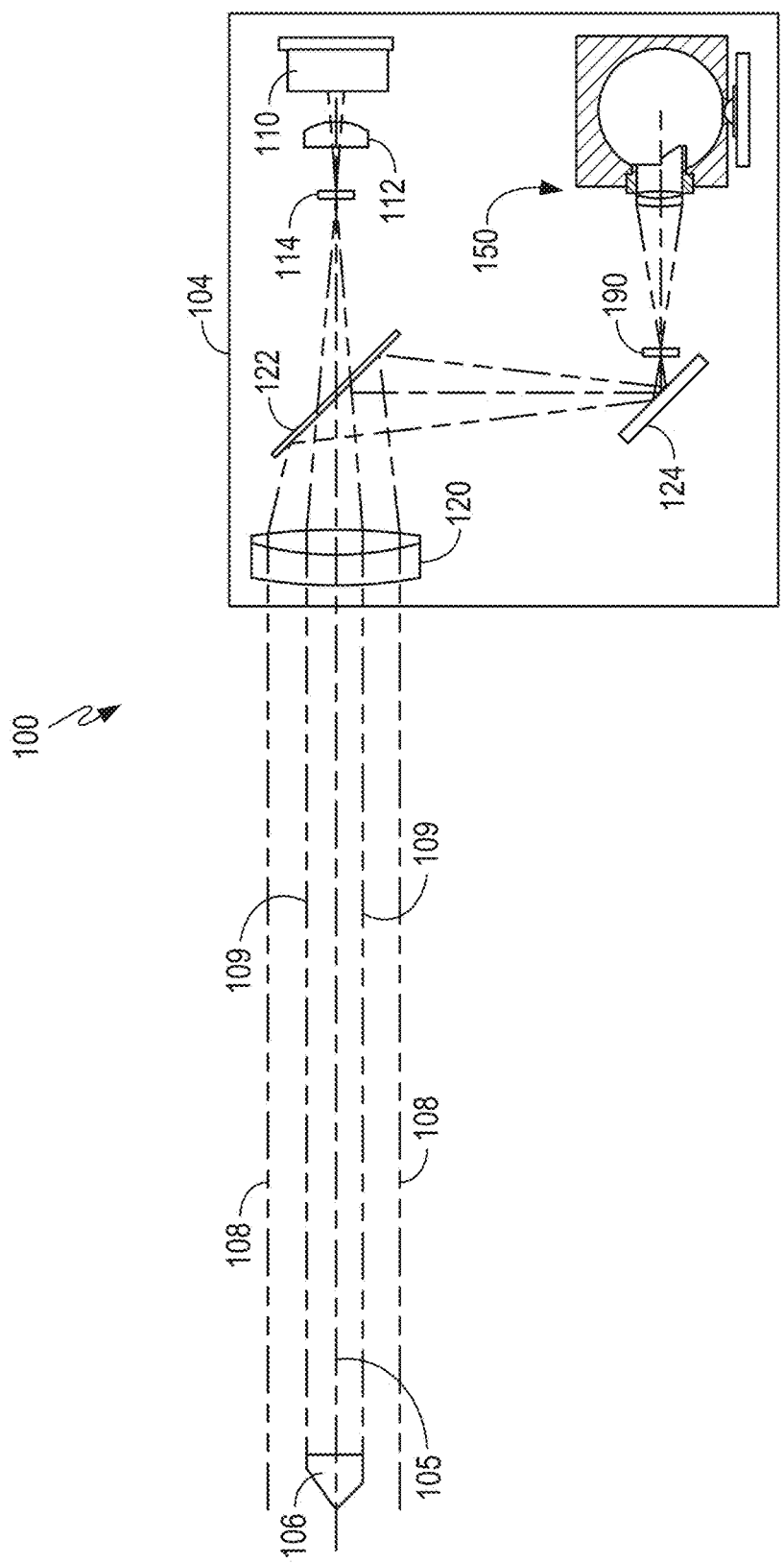
FIG. 10 is a schematic diagram of an optical sub-system of a double-pass opacity monitor.

Referring to FIG. 10, an opacity monitor 100 comprises a transceiver assembly 104 and a retroreflector assembly 106. The transceiver assembly 104 is configured to project an output light beam 108 to the retroreflector assembly 106. The retroreflector assembly 106 is configured to reflect the projected output light beam 108 back to the transceiver assembly 104 as a return light beam 109 when the transceiver assembly 104 and the retroreflector assembly 106 are optically aligned along a central alignment axis 105. The transceiver assembly 104 comprises a sensor 110 configured to detect the intensity of the projected and reflected return light beam 109. The transceiver assembly 104 also comprises a light projection assembly 150 configured to produce the output light beam 108. The light projection assembly 150 comprises an integrating sphere comprising an input aperture, an output aperture, and a spherical-shaped internal chamber (see, e.g., FIGS. 5A-9). An LED source is located external to the chamber at the input aperture (see, e.g., FIGS. 5A-9). A light baffle is located within the chamber at the output aperture (see, e.g., FIGS. 5A-9). A condenser lens is located external to the chamber at the output aperture (see, e.g., FIGS. 5A-9).

The light projection assembly 150 further comprises a projection aperture 190. The transceiver assembly 104 further comprises a receiver lens 112, a receiver aperture 114, a projection lens 120, a beamsplitter 122, and a mirror 124. The projection lens 120 is optically aligned with the projection aperture 190 of the light projection assembly 150 through the mirrors 122 and 124. The light exiting through the projection aperture 190 is reflected by the mirrors 122 and 124 into the projection lens 120. The projection lens 120 is configured to focus the light beam produced by the light projection assembly 150 and project the light beam as the output beam 108. The receiver aperture 114 is configured to receive the return light beam 109 reflected by the retroreflector assembly 106. The receiver lens 112 is located between the receiver aperture 114 and the sensor 110. The receiver lens 112 is configured to focus the return light beam 109 reflected by the retroreflector assembly 106 onto the sensor 110.

Figure 11:
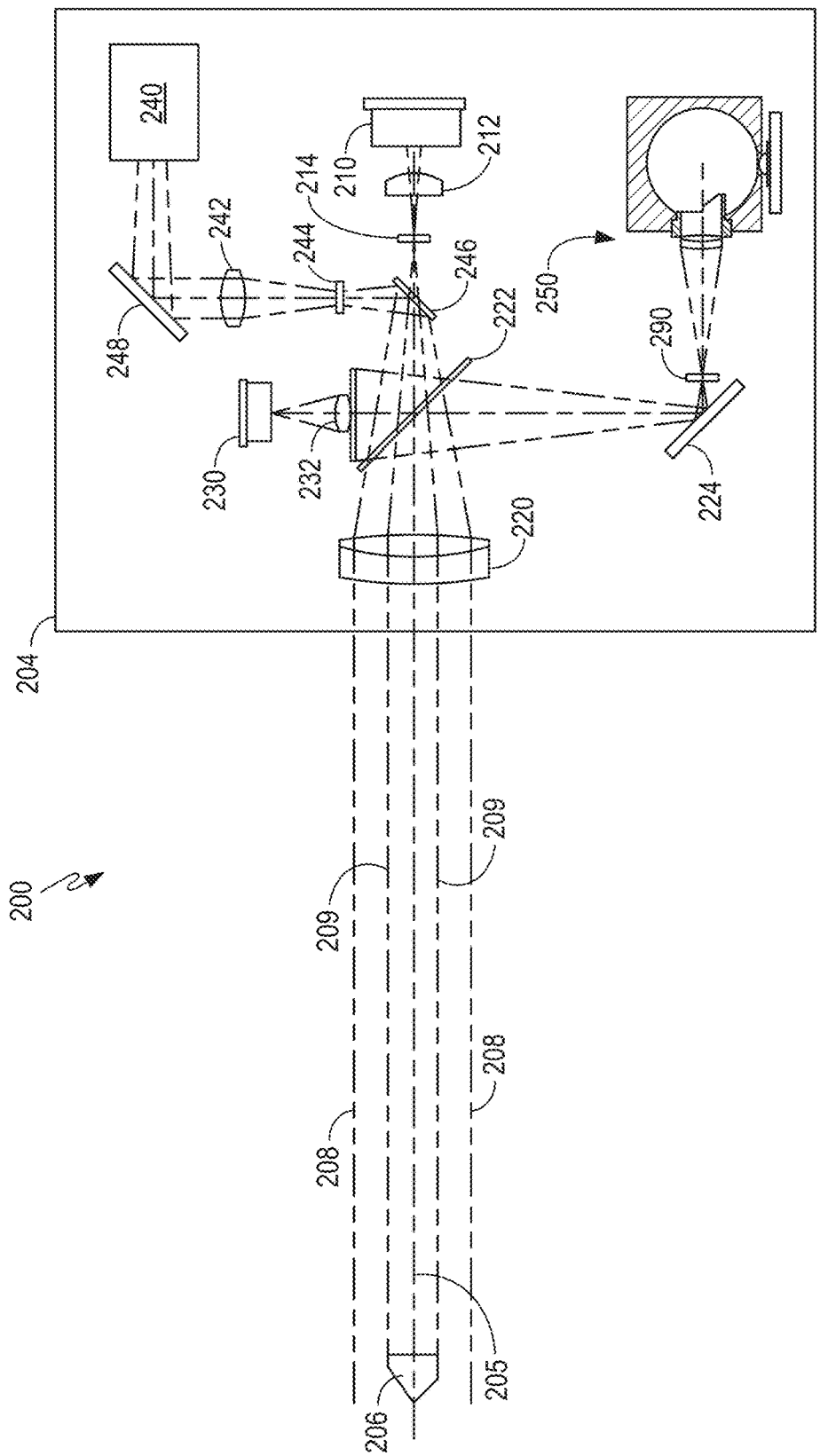
FIG. 11 is a schematic diagram of an optical sub-system of a double-pass opacity monitor including alignment optics.
Figure 12:
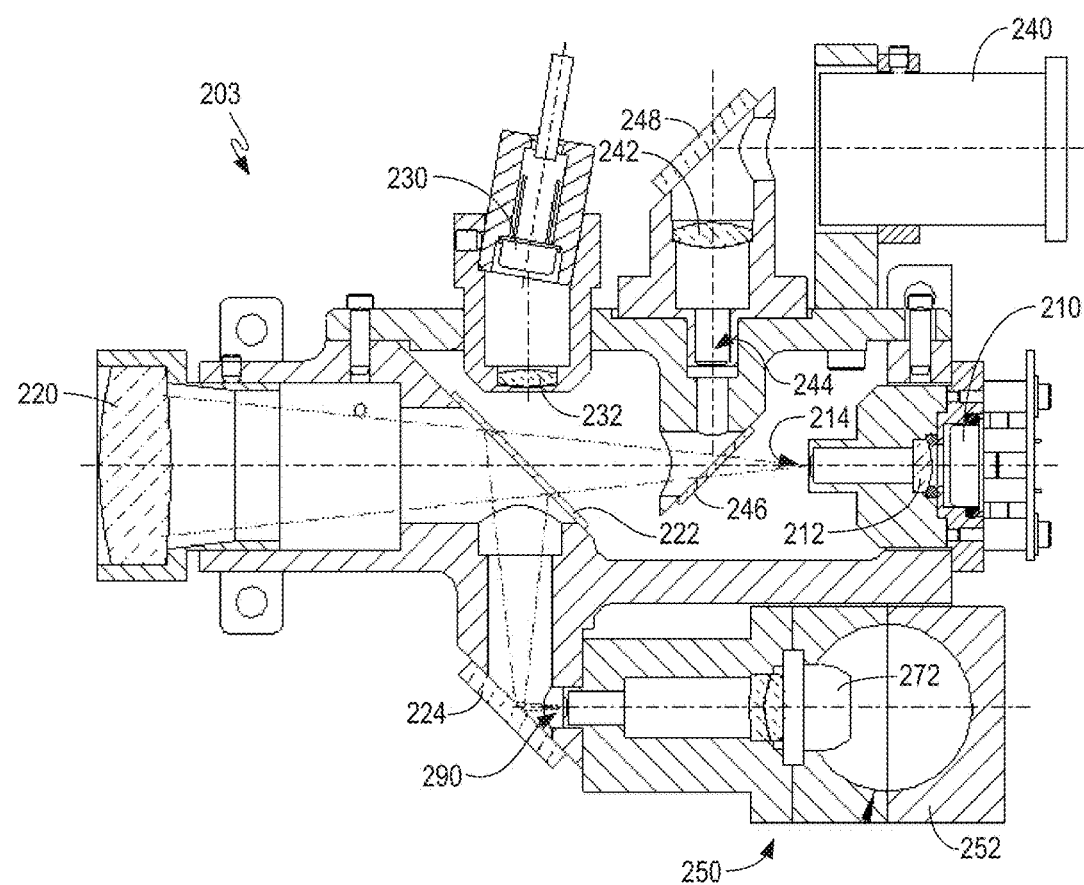
FIG. 12 is a cross-sectional side view of an optical sub-system of a double-pass opacity monitor.
Figure 13:
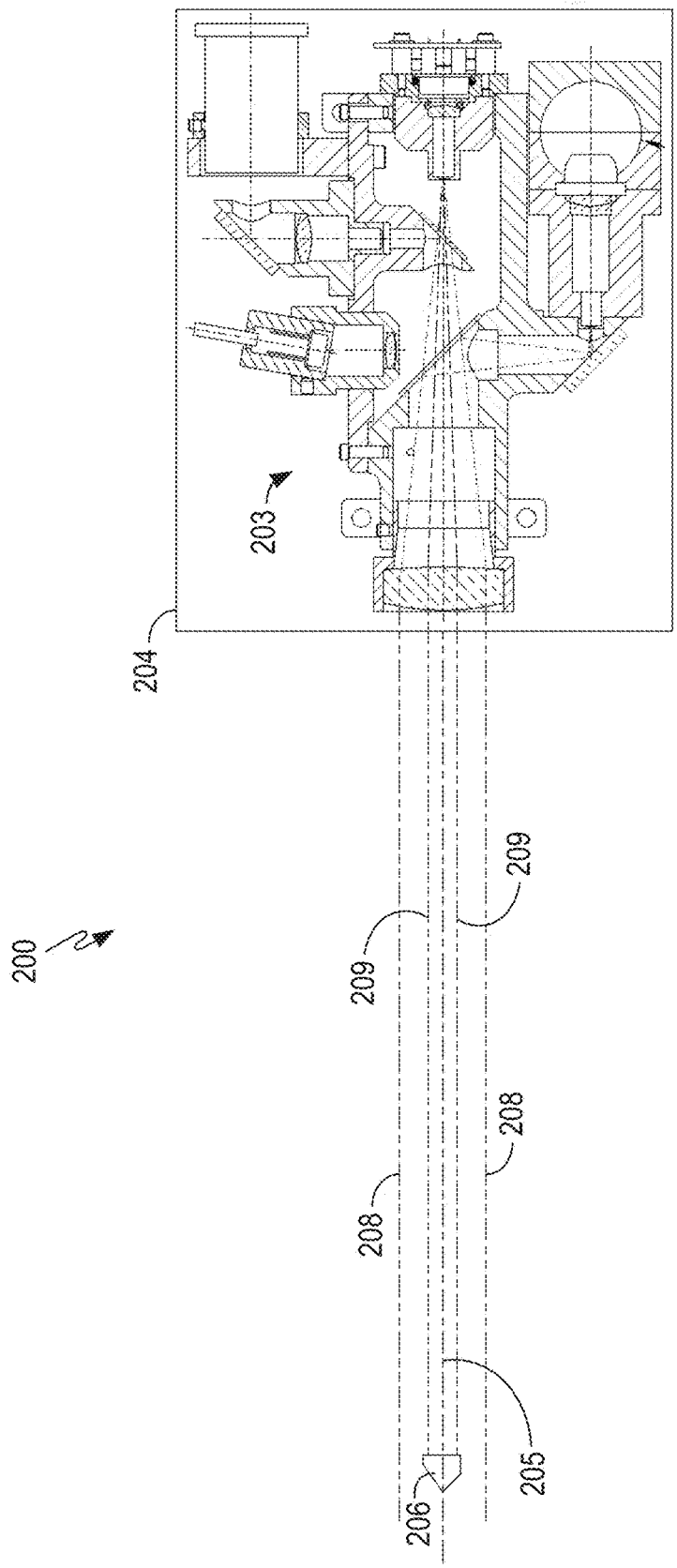
FIG. 13 is a cross-sectional side view schematic diagram of an optical sub-system of a double-pass opacity monitor.

Referring to FIGS. 11-13, an opacity monitor 200 comprises a transceiver assembly 204 and a retroreflector assembly 206. The transceiver assembly 204 is configured to project an output light beam 208 to the retroreflector assembly 206. The retroreflector assembly 206 is configured to reflect the projected output light beam 208 back to the transceiver assembly 204 as a return light beam 209 when the transceiver assembly 204 and the retroreflector assembly 206 are optically aligned along a central alignment axis 205. The transceiver assembly 204 comprises a sensor 210 configured to detect the intensity of the projected and reflected return light beam 209. The transceiver assembly 204 also comprises a light projection assembly 250 configured to produce the output light beam 208. The light projection assembly 250 comprises an integrating sphere 252 comprising an input aperture, an output aperture, and a spherical-shaped internal chamber (see, e.g., FIGS. 5A-9). An LED source is located external to the chamber at the input aperture (see, e.g., FIGS. 5A-9). A light baffle 272 is located within the chamber at the output aperture (see, e.g., FIGS. 5A-9). A condenser lens is located external to the chamber at the output aperture (see, e.g., FIGS. 5A-9).

The light projection assembly 250 further comprises a projection aperture 290. The transceiver assembly 204 further comprises a receiver lens 212, a receiver aperture 214, a projection lens 220, a first beamsplitter 222, a first mirror 224, a reference sensor 230, a reference lens 232, an eyepiece 240, an eyepiece lens 242, an eyepiece aperture 244, a second beamsplitter 246, and a second mirror 248.

The projection lens 220 is optically aligned with the projection aperture 290 of the light projection assembly 250 through the first mirror 224 and the first beamsplitter 222. The light exiting through the projection aperture 290 is reflected by the first mirror 224 and the first beamsplitter into the projection lens 220. The projection lens 220 is configured to focus the light beam produced by the light projection assembly 250 and project the light beam as the output beam 208. The first beamsplitter 222 also passes a portion of the light exiting through the projection aperture 290 and reflected by the first mirror 224 which further passes through the reference lens 232 and into the reference sensor 230. The reference sensor 230 controls the intensity of the output beam 208 used for determination of opacity values.

The projection lens 220 focuses the return beam 209 through the receiver aperture 214, which is configured to receive the return light beam 209. The receiver lens 212 is located between the receiver aperture 214 and the sensor 210. The receiver lens 212 is configured to focus the return beam 209 onto the sensor 210. The difference between the intensity of the return beam 209, as measured by the sensor 210 during clear conditions (no particulates present), and the intensity of the return beam 209, as measured by the sensor 210 when particulates are present in the gas stream in a stack or other conduit, provides the opacity value of any particulate-containing gasses located between the transceiver assembly 204 and the retroreflector assembly 206 (see, e.g., FIG. 1).

The second beamsplitter 246 is located between the first beamsplitter 222 and the receiver aperture 214. The second beamsplitter 246 reflects a portion of the return beam 209 through the eyepiece aperture 244 and the eyepiece lens 242. The eyepiece lens 242 focuses the portion of return beam 209 that is reflected by the second beamsplitter 246 onto the second mirror 248, which reflects the beam into the eyepiece 240. The eyepiece 240 allows installers and/or operators of the opacity monitor 200 to ensure alignment of the transceiver assembly 204 and the retroreflector assembly 206.

Referring to FIGS. 12 and 13, an exemplary optical sub-system 203 of a transceiver assembly 204 of an opacity monitor 200 is shown. The optical sub-system 203 comprises the components described above in connection with FIG. 11. Although the opacity monitors 100 and 200 shown in FIGS. 10, 11, and 13 are double-pass opacity monitors, it is nevertheless understood that the light projection assemblies described in this specification may be used in either single-pass or double-pass opacity monitors. For example, the light projection assemblies described in this specification may be used in opacity monitors as described in U.S. Pat. Nos. 4,937,461; 5,077,480; 5,617,212; 5,751,423; 5,831,730; 5,999,257; 6,781,695; and 7,715,009, which are each incorporated by reference into this specification. Moreover, it is understood that the light projection assemblies described in this specification may be used in any other applications in which the projection of uniform light beams is advantageous.

Various features and characteristics of the invention are described in this specification and illustrated in the drawings to provide an overall understanding of the disclosed devices, assemblies, and systems. It is understood that the various features and characteristics described in this specification and illustrated in the drawings can be combined in any suitable manner regardless of whether such features and characteristics are expressly described or illustrated in combination in this specification. The Inventors and the Applicant expressly intend such combinations of features and characteristics to be included within the scope of this specification. As such, the claims can be amended to recite, in any combination, any features and characteristics expressly or inherently described in, or otherwise expressly or inherently supported by, this specification. Furthermore, the Applicant reserves the right to amend the claims to affirmatively disclaim features and characteristics that may be present in the prior art, even if those features and characteristics are not expressly described in this specification. Therefore, any such amendments will not add new matter to the specification or claims, and will comply with written description, sufficiency of description, and added matter requirements (e.g., 35 U.S.C. § 112(a) and Article 123(2) EPC). The devices, assemblies, and systems described in this specification can comprise, consist of, or consist essentially of the various features and characteristics described in this specification.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and can be employed or used in an implementation of the described processes, compositions, and products. Further, the use of a singular noun includes the plural, and the use of a plural noun includes the singular, unless the context of the usage requires otherwise.

What is claimed is:

1. A light projection assembly, comprising:
an integrating sphere defining an input aperture, an output aperture, and a spherical-shaped internal chamber;
an LED source located external to the spherical-shaped internal chamber at the input aperture, wherein the LED source is configured to emit light through the input aperture into the spherical-shaped internal chamber;
a light baffle surrounding a portion of the output aperture, wherein the light baffle extends into the spherical-shaped internal chamber to prevent light emitted by the LED source from exiting directly through the output aperture; and
a condenser lens located external to the spherical-shaped internal chamber at the output aperture, wherein the condenser lens is configured to collect light reflected within the spherical-shaped internal chamber that exits through the output aperture.

2. The light projection assembly of claim 1, wherein the input aperture defines an input area, the output aperture defines an output area, and a sum of the input area and the output area is less than 5% of a total surface area of the spherical-shaped internal chamber.

3. The light projection assembly of claim 1, wherein the input aperture defines an input axis, the output aperture defines an output axis, and the input axis is perpendicular to the output axis.

4. The light projection assembly of claim 3, wherein the light baffle extends into the spherical-shaped internal chamber parallel to the output axis.

5. The light projection assembly of claim 1, wherein the light baffle defines a semi-cylindrical shaped surface that surrounds the portion of the output aperture.

6. The light projection assembly of claim 1, further comprising a baffle ring located through a wall of the integrating sphere, wherein the output aperture extends through the baffle ring, and wherein the light baffle is integrally formed on the baffle ring.

7. The light projection assembly of claim 1, wherein the light baffle is integrally formed on an internal surface of the spherical-shaped internal chamber.

8. The light projection assembly of claim 1, further comprising a projection housing attached to an external surface of the integrating sphere adjacent to the output aperture, the projection housing defining a lens opening, a projection aperture, and an internal channel between the lens opening and the projection aperture, wherein the condenser lens is at least partially located in the lens opening and optically aligned with the output aperture and the projection aperture to focus the collected light through the projection aperture.

9. The light projection assembly of claim 1, wherein the integrating sphere comprises a material of construction comprising sintered poly(tetrafluoroethylene).

10. An opacity monitor comprising the light projection assembly of claim 1.

11. An opacity monitor, comprising:
a retroreflector assembly; and
a transceiver assembly configured to project an output light beam to the retroreflector assembly, wherein the retroreflector assembly is configured to reflect the projected output light beam back to the transceiver assembly as a return light beam when the transceiver assembly and the retroreflector assembly are optically aligned along a central axis, the transceiver assembly comprising:
  a sensor configured to detect an intensity of the reflected return light beam; and
  a light projection assembly, comprising:
    an integrating sphere defining an input aperture, an output aperture, and a spherical-shaped internal chamber;
    an LED source located external to the spherical-shaped internal chamber at the input aperture, wherein the LED source is configured to emit light through the input aperture into the spherical-shaped internal chamber;
    a light baffle surrounding a portion of the output aperture, wherein the light baffle extends into the spherical-shaped internal chamber to prevent light emitted by the LED source from exiting directly through the output aperture; and
    a condenser lens located external to the spherical-shaped internal chamber at the output aperture, wherein the condenser lens is configured to collect light reflected within the spherical-shaped internal chamber that exits through the output aperture;
  wherein the transceiver assembly is configured to use the collected light to produce the projected output light beam, and
  wherein opacity values measured by the opacity monitor vary by no greater than ±0.5% opacity when the transceiver assembly or the retroreflector assembly is angularly misaligned by up to ±0.25 degrees from the central axis at a distance of 3 meters between the transceiver assembly and the retroreflector assembly.

12. The opacity monitor of claim 11, wherein the input aperture defines an input area, the output aperture defines an output area, and a sum of the input area and the output area is less than 5% of a total surface area of the spherical-shaped internal chamber.

13. The opacity monitor of claim 11, wherein the input aperture defines an input axis, the output aperture defines an output axis, the input axis is perpendicular to the output axis, and the light baffle extends into the spherical-shaped internal chamber parallel to the output axis.

14. The opacity monitor of claim 11, wherein the light baffle defines a semi-cylindrical shaped surface that surrounds the portion of the output aperture.

15. The opacity monitor of claim 11, wherein the light projection assembly further comprises a baffle ring located through a wall of the integrating sphere, wherein the output aperture extends through the baffle ring, and wherein the light baffle is integrally formed on the baffle ring.

16. The opacity monitor of claim 11, wherein the light projection assembly further comprises a projection housing attached to an external surface of the integrating sphere adjacent to the output aperture, the projection housing defining a lens opening, a projection aperture, and an internal channel between the lens opening and the projection aperture, wherein the condenser lens is at least partially located in the lens opening and optically aligned with the output aperture and the projection aperture to focus the collected light through the projection aperture.

17. The opacity monitor of claim 16, wherein the transceiver assembly further comprises a projection lens optically aligned with the projection aperture of the light projection assembly, and wherein the projection lens is configured to focus the collected light to produce the projected output light beam.

18. The opacity monitor of claim 11, wherein the integrating sphere comprises a material of construction comprising sintered poly(tetrafluoroethylene).

19. The opacity monitor of claim 11, wherein the transceiver assembly further comprises a receiver aperture configured to receive the reflected return light beam.

20. The opacity monitor of claim 19, wherein the transceiver assembly further comprises a receiver lens located between the receiver aperture and the sensor, and wherein the receiver lens is configured to focus the reflected return light beam onto the sensor.

* * * * *